United States Patent

Kawashima et al.

Patent Number: 5,547,952
Date of Patent: Aug. 20, 1996

[54] 3-OXO-1,4-BENZOTHIAZINE DERIVATIVES

[75] Inventors: Yoichi Kawashima, Kyoto; Atsutoshi Ota, Osaka; Yuko Morikawa, Neyagawa; Hiroyuki Mibu, Osaka, all of Japan

[73] Assignee: Santen Pharmaceutical Co., Ltd., Osaka, Japan

[21] Appl. No.: 347,043

[22] Filed: Nov. 30, 1994

[30] Foreign Application Priority Data

Dec. 9, 1993 [JP] Japan ................................ 5-309131

[51] Int. Cl.$^6$ .................... C07D 279/16; A61K 31/54
[52] U.S. Cl. ........................ 514/224.2; 544/52; 514/90
[58] Field of Search ................... 514/224.2, 90; 544/52

[56] References Cited

U.S. PATENT DOCUMENTS 3,923,709  12/1975  Worley ..................... 260/243
4,078,062  3/1978  Krapcho ..................... 424/246

FOREIGN PATENT DOCUMENTS 0116368  8/1984  European Pat. Off. .
0163551  12/1985  European Pat. Off. .
9405647  3/1994  WIPO .

OTHER PUBLICATIONS

Chemical Abstracts, vol. 112, No. 23, Jun. 4, 1990, Abstract No. 216950 M. Takakazu et al "Preparation of 3–oxo–1, 4–benzothiazine derivatives for removal of active oxygen species and for inhibition of lipid peroxide formation" of JP–A–89 287 077 (1989).

Primary Examiner—John M. Ford
Attorney, Agent, or Firm—Frishauf, Holtz, Goodman, Langer & Chick, P.C.

[57] ABSTRACT

This invention relates to the compounds of the formula [I] which are useful for the treatment of cataracts, and the synthetic intermediates of the formula [II],

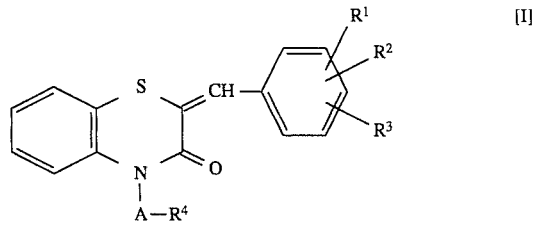

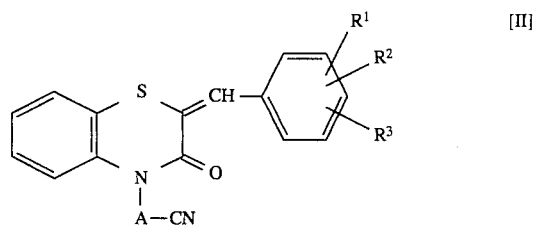

wherein $R^1$ is hydroxy which can be protected by a protective group;

$R^2$ is lower alkyl;

$R^3$ is hydrogen, lower alkyl, hydroxy, which can be protected by a protective group, or lower alkoxy, and the said lower alkyl can be substituted by hydroxy, which can be protected by a protective group, amino or lower alkylamino;

$R^4$ is tetrazolyl, phosphonol or lower alkyl ester thereof, or sulfonyl or lower alkyl ester thereof, and A is alkylene.

15 Claims, No Drawings

3-OXO-1,4-BENZOTHIAZINE DERIVATIVES

FIELD OF THE INVENTION

This invention relates to novel 3-oxo-1,4-benzothiazine derivatives which have protein stabilizing effect and suppressive effect on lipid peroxide formation, and are useful for treatment of cataracts etc.

BACKGROUND OF THE INVENTION

The formation of cataracts is an intractable eye condition where an opacification of the lens is caused and which results in a loss of visual acuity. Various studies on a causal factor and mechanism of cataracts, and a treatment method therefor have been made. But at present, there are very few medical substances which are effective for cataracts.

It is reported that an increase of peroxide in the lens is related to a cause of cataracts and a chemical substance having suppressive effect on lipid peroxide formation is effective on treatment of cataracts (Current Eye Res., 5, 37 (1986)). It is also reported that protein denaturation is observed in lenses of cataract patients (Ophthalmology, 19, 1283 (1977)).

From the reports, a chemical substance which has suppressive effect on lipid peroxide formation in combination with protein stabilizing effect can be presumed to be especially useful for treatment of cataracts. A compound having the above both effects, however, has not been studied and the development of such a compound has been desired.

As the result of our precise study to find a compound having a suppressive effect on lipid peroxide formation in combination with a protein stabilizing effect, the inventors found that 3-oxo-1,4-benzothiazine derivatives, in which the 2nd-position was substituted by a benzylidene group and the 4th-position was substituted by an acidic group, which is tetrazolyl, phosphonyl or sulfonyl, and the phenyl ring of the benzylidene group was further substituted by hydroxy and lower alkyl groups, exhibited both effects.

Some of 3-oxo-1,4-benzothiazine derivatives having a benzylidene substituent at the 2nd-position, where the chemical structure is common to the basic structure of the compounds of this invention, were reported to show activitity as a herbicide (U.S. Pat. No. 3923709), a tranquilizer (Japanese Patent Publication No. 10671/1974) or a synthetic intermediate of benzothiazepine derivatives (Japanese Unexamined Patent Publication No. 72875/1985). The description in the publications, however, is limited to benzothiazine derivatives wherein the 4-th position of the benzothiazine ring is substituted by aminoalkyl or carboxyalkyl. Benzothiazine derivatives having an acidic substituent, except carboxy group, have not been reported. Further the prior art discloses neither a protein stabilizing effect nor a suppressive effect on lipid peroxide formation.

Japanese Unexamined Patent Publication No. 287077/1989 discloses2-benzylidene-3-oxo-1,4-benzothiazine derivatives which have an active oxygen elimination effect or a suppressive effect on lipid peroxide formation. In this publication, however, the substituent at the 4th-position is limited to a lower alkyl group and a protein stabilizing effect is not disclosed at all.

In the meantime, recently the utility of aldose reductase inhibitors for treatment of cataract has attracted attention. The compound of this invention also has an aldose reductase inhibiting effect and is very useful for the treatment of cataracts.

DETAILED DESCRIPTION OF INVENTION

This invention relates to the compounds of the formula [I] and salts thereof (hereinafter called the compounds of this invention), pharmaceutical use for treatment of cataracts and synthetic intermediates of the formula [II] (hereinafter called the intermediates of this invention).

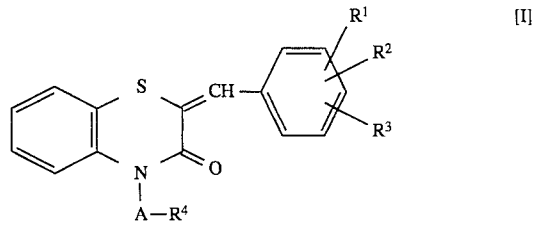

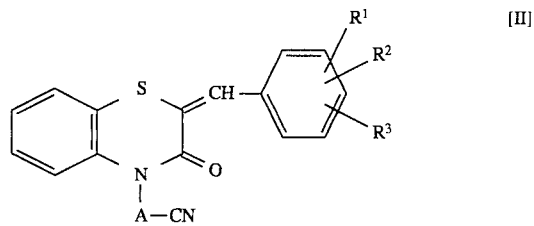

wherein $R^1$ is hydroxy which can be protected by a hydroxy protective group;

$R^2$ is lower alkyl;

$R^3$ is hydrogen, lower alkyl, hydroxy, which can be protected by a hydroxy protective group, or lower alkoxy, and the said lower alkyl can be substituted by hydroxy, which can be protected by a hydroxy protective group, amino or lower alkylamino;

$R^4$ is tetrazolyl, phosphono or lower alkyl ester thereof, or sulfonyl or lower alkyl ester thereof, and A is alkylene. The same shall be applied hereinafter.

The terms defined above are explained as follows in more detail.

The term "lower alkyl" means straight or branched alkyl having 1 to 6 carbon atoms exemplified by methyl, ethyl, propyl, hexyl, isopropyl, tert.-butyl and (dimethyl)ethyl.

The term "lower alkoxy" means straight or branched alkoxy having 1 to 6 carbon atoms exemplified by methoxy, ethoxy, propoxy, hexyloxy, isopropoxy and tert.-butoxy.

The term "alkylene" means alkylene having 1 to 10 carbon atoms exemplified by methylene, ethylene, propylene, tetramethylene, hexamethylene, heptamethylene, decamethylene, (dimethyl)methylene and (diethyl)methylene.

The term "hydroxy protective group" means a group widely used for protection of a hydroxy group, for example, lower alkylsulfonyl exemplified by methanesulfonyl; arylsulfonyl exemplified by phenylsulfonyl and p-toluenesulfonyl; lower alkanoyl exemplified by acetyl, propionyl and pivaloyl; lower alkoxymethyl exemplified by methoxymethyl; benzoyl; benzyloxymethyl; tetrahydropyranyl, or trimethylsilyl.

The term "aryl" means aromatic hydrocarbon exemplified by phenyl, tolyl, xylyl and mesityl.

Examples of the pharmaceutically acceptable salts in this invention are alkali metal salts or alkaline earth metal salts exemplified by sodium, potassium and calcium salts, ammonium salt, organic amine salts exemplified by diethylamine and triethanolamine salts, or salts of inorganic acid exemplified by hydrochloric acid, sulfuric acid and nitric acid.

Typical synthetic methods of the compounds of this invention are shown in the following 1)–3).

1) Synthesis of a compound having a tetrazolyl group as a substituent $R^4$.

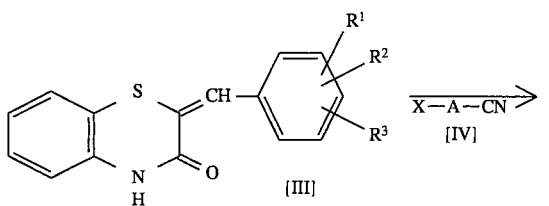

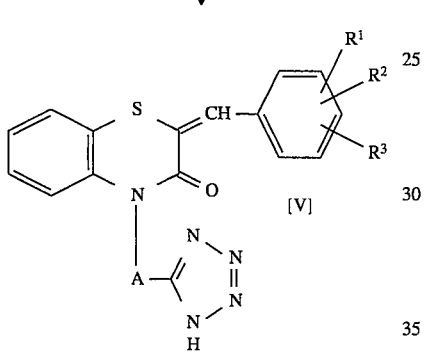

wherein X is halogen, alkylsulfonyl or arylsulfonyl. The same definition applies to the reaction below. The compound of the formula [II] can be prepared by a reaction of the compound of the formula [III] with the compound [IV]. The compound of the formula [II] is further reacted with sodium azide to give the compound of this invention represented by the formula [V] wherein $R^4$ is tetrazolyl. The compound of the formula [II] is also a novel compound which is especially useful as a synthetic intermediate to introduce a tetrazolyl group into $R^4$.

In another way, the compound of the formula [III] can be synthesized according to the method described in Japanese Unexamined Patent Publication No. 287077/1989. The typical synthetic route is shown below.

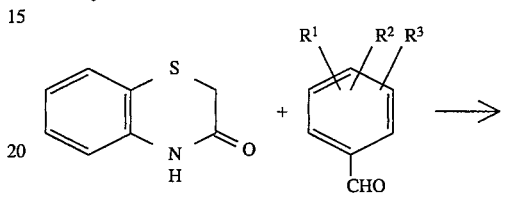

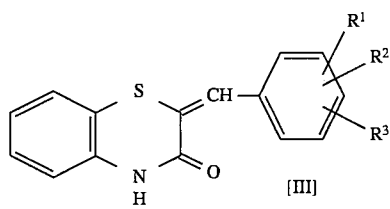

2) Synthesis of a compound having a phosphono group or lower alkyl ester thereof as a substituent $R^4$.

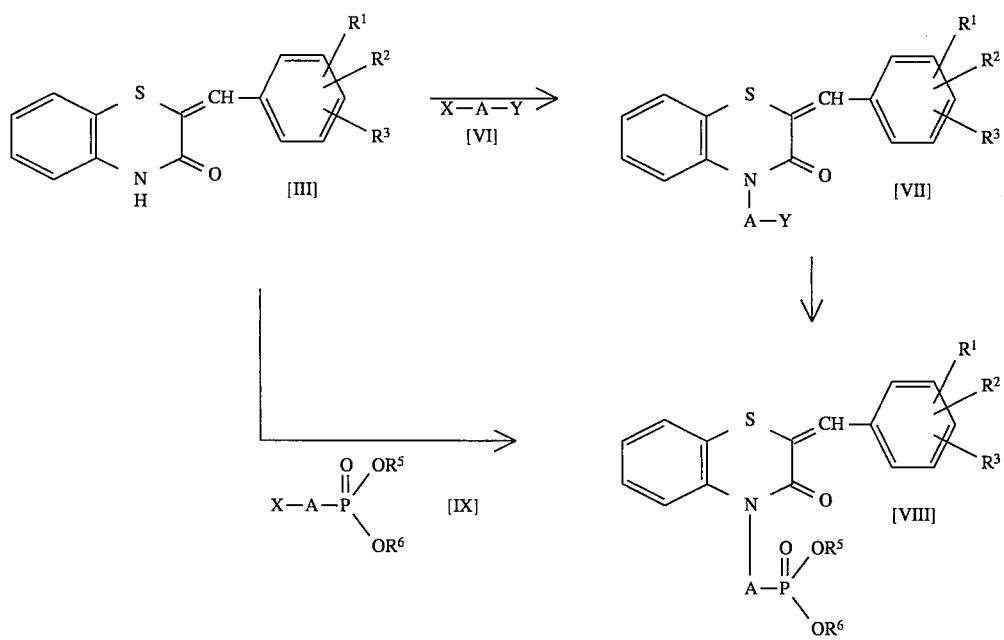

wherein Y is lower alkoxy, and $R^5$ or $R^6$ is the same or different and each is hydrogen or lower alkyl.

The compound of the formula [VIII] can be prepared by a reaction of the compound of the formula [III] with the compound of the formula [VI] in a presence of base. The compound of the formula [VII] is reacted with trimethylsilyl halide and followed by a reaction with trialkyl phosphite to give the compound of this invention wherein $R^4$ is phosphonyl or lower alkyl ester thereof, which is represented by the formula [VIII].

In another way, the compound of this invention represented by the formula [VIII] can be prepared by a reaction of the compound of the formula [III] with the compound of the formula [IX] in a presence of base.

3) Synthesis of a compound having a sulfonyl group or lower alkyl ester thereof as a substituent $R^4$.

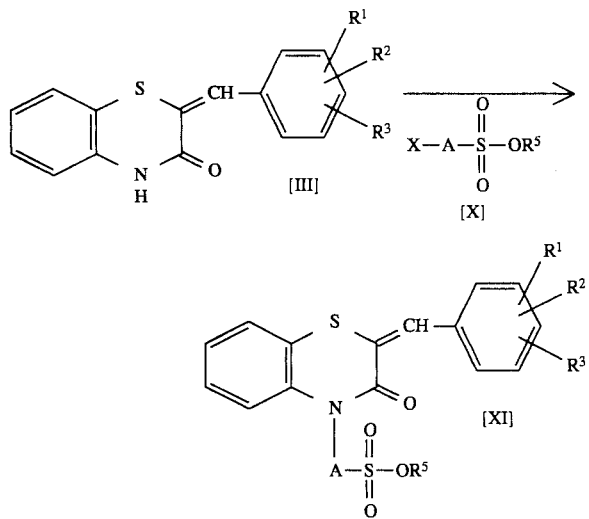

The compound of this invention wherein $R^4$ is sulfonyl or lower alkyl ester thereof, which is represented by the formula [XI], can be prepared by a reaction of the compound of the formula [III] with the compound of the formula [X].

A hydroxy group substituted on the phenyl ring of the benzylidene group may be protected by any of the above-mentioned protective groups by the usual method before or after the above-mentioned synthetic process, and the protective group can be removed by any usual method.

A phosphono or sulfonyl group substituted in the 4-th position of benzothiazine can be converted into a lower alkyl ester before or after the above-mentioned synthetic process by any usual method.

On the other hand, a lower alkyl ester can be hydrolyzed to a phosphonic acid or sulfonic acid by any usual method.

The compounds prepared by the above methods can be converted into their salts as mentioned before by any usual method.

The compounds and intermediates of this invention have stereoisomers or optical isomers, and these isomers are also included in this invention. For example, the compounds and intermediates of this invention have Z-form or E-form because of the existence of benzylidene group, and these forms are included in this invention.

A compound which has a suppressive effect on lipid peroxide formation in combination with a protein stabilizing effect can be presumed to be especially useful for treatment of cataracts. A compound having both of these effects, however, has not been studied and development of such a compound is desirable.

Based on the information that 3-oxo-1,4-benzothiazine derivatives having benzylidene substituent at the 2nd-position have suppressive effect on lipid peroxide formation (Japanese Unexamined Patent Publication No. 287077/1989), the inventors focused attention on compounds having 2-benzylidene-3-oxo-1,4-benzothiazine as a basic structure and started a study to solve the above-mentioned problem.

First, the inventors considered the information that toluene derivatives, in which hydroxy and tert.-butyl groups substituted, have anti-oxidizing effect. An anti-oxidizing agent exhibits a suppressive effect on lipid peroxide formation. Accordingly the inventors studied how substituents effect a suppressive effect on lipid peroxide formation, by introducing various kinds of substituents such as alkyl and hydroxy into the phenyl ring of a benzylidene group. As the result of the study, it was found that compounds having an excellent suppressive effect on lipid peroxide formation could be obtained by introducing hydroxy and lower alkyl groups into the phenyl ring of a benzylidene group. But, 2-benzylidene-3-oxo-1,4-benzothiazine compounds substituted by a lower alkyl group at the 4th-position did not have a protein stabilizing effect, which is another necessary property in this invention. Therefore it was recognized that the substituent at the 4th-position exerted an influence on the protein stabilizing effect.

Accordingly the inventors synthesized novel compounds having various kinds of substituents at the 4th-position of 1,4-benzothiazine, and carried out investigations to find a compound having a protein stabilizing effect. As the result of the investigations, the inventors found that a compound having an alkyl group which was further substituted by tetrazolyl, phosphonyl or sulfonyl at the 4th-position, exhibited a protein stabilizing effect.

From these studies, the inventors found that 2-benzylidene-3-oxo-1,4-benzothiazine compounds, wherein the 4th-position was substituted by an alkyl group having an acidic moiety, that is, tetrazolyl, phosphonol or sulfonyl, and wherein the phenyl ring of the benzylidene group was further substituted by hydroxy and lower alkyl groups, showed an excellent suppressive effect on lipid peroxide formation in combination with a protein stabilizing effect. That is to say, the fundamental components of a compound according to this invention are (i) the 4th-position of 3-oxo-1,4-benzothiazine is substituted by an alkyl group having an acidic moiety, that is, tetrazolyl, phosphono or sulfonyl, (ii) the 2nd-position is substituted by a benzylidene group, and (iii) the phenyl ring of the benzylidene group is further substituted by at least one hydroxy group and one lower alkyl group.

In the case of a medicament, conversion of the phosphono group or sulfonyl group into an ester or protection of the hydroxy group by a suitable protective group is generally applied to make pro-drugs in order to enhance the absorption or improve the duration of the medicament in the living body, or to make a compound stable. Furthermore, such techniques are generally used for manufacturing drugs. In other words, such a derived compound is generally used as a synthetic intermediate. Therefore in this invention, hydroxy groups may be protected by the widely used protective group for hydroxy, and phosphono groups or sulfonyl groups may be converted into esters.

The characteristic structure of the compound of this invention is that explained above, but a preferable example of the substituent at the phenyl ring of the benzylidene group is explained as follows: a hydroxy group substitutes at the 4th-position, more preferably, lower alkyl group(s) substitute(s) at least one vicinal position of a hydroxy substituent.

That is to say, it is preferable that lower alkyl group(s) substitute(s) at the 3rd-position or at both the 3rd- and 5th-positions. More preferable examples of the lower alkyl group are methyl or tert.-butyl.

In order to examine the effect of the compound of this invention initially, an experiment to examine protein stabilizing effect was performed using bovine serum albumin. Details are shown in the article of Pharmacological Test described later in this specification.

The inventors found that the compound of this invention had an excellent protein stabilizing effect, however, the compound which has different substituents in spite of the same basic structure as the compound of this invention, namely, 1,4-benzothiazine derivative having lower alkyl substituent at the 4th-position described in Japanese Unexamined Patent Publication No. 287077/1989, did not have a protein stabilizing effect.

Secondly, in order to examine the suppressive effect on lipid peroxide formation of the compounds of this invention, an experiment was performed using microsomes of rat liver. As the result of the experiment, it was found that the compound of this invention had an excellent suppressive effect on lipid peroxide formation.

From the results of the above pharmacological tests, it was found that the compounds of this invention had a suppressive effect on lipid peroxide formation in combination with a protein stabilizing effect, and was useful for the treatment of cataract.

In addition, it is also reported that a chemical substance which has a suppressive effect on lipid peroxide formation or a protein stabilizing effect is applicable to an anti-inflammatory (Lancet, 1, 169 (1965), Biochem. Biophys. Acta., 489, 163 (1977)). Therefore it is expected that the compound of this invention is also useful as an anti-inflammatory.

Furthermore, an experiment was carried out according to the report of Karo et al. (Chem. Pharm. Bull., 33, (1) 74–83 (1985)), and it was also found that the compounds of this invention had an aldose reductase inhibiting effect. This result further supports the conclusion that the compounds of this invention are excellent therapeutic agents for cataract treatment and they are also expected to be useful for treatment of diabetic complications.

The compounds of this invention can be administered orally or parenterally. Examples of dosage forms are tablet, capsule, granule, powder, injection, ophthalmics, etc. The preparations can be prepared by the usual methods. For example, oral preparations such as a tablet, a capsule, a soft capsule and granules can be produced, if necessary, by adding diluents such as lactose, starch, crystalline cellulose or vegetable oil; lubricants such as magnesium stearate or talc; binders such as hydroxypropylcellulose or polyvinylpyrrolidone; a disintegrator such as carboxymethylcellulose calcium, or a coating agent such as hydroxypropylmethylcellulose. Ophthalmics can be prepared by adding a tonicity agent such as sodium chloride; a buffer such as sodium phosphate; a solubilizer such as polysorbate 80, or preservatives such as benzalkonium chloride.

The dosage is adjusted depending on symptoms, age, dosage form, etc., but in the case of oral preparations, the usual daily dosage is 1 to 5000 mg, preferably 1 to 1000 mg, which can be given in one or a few divided doses. In the case of ophthalmics, the dosage is 0.001 to 10%, preferably 0.01 to 3%, and one to several drops can be instilled per day.

Examples of preparations and formulations of the compounds of this invention are shown below. These examples do not limit the scope of this invention, but are intended to make this invention more clearly understandable.

EXAMPLE

Example 1

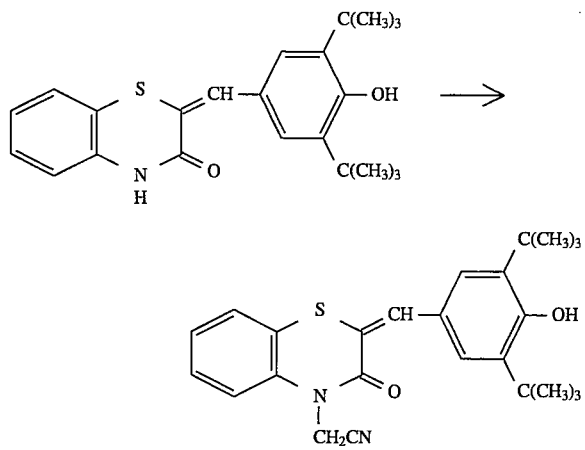

2-(3,5-Di-tert.-butyl-4-hydroxybenzylidene)-4-cyanomethyl-3, 4-dihydro-3-oxo-2H-1,4-benzothiazine (compound No. 1-1)

To a suspension of sodium hydride (60% suspension in paraffin liquid, 0.22 g) in tetrahydrofuran (2 ml), 2-(3,5-di-tert.-butyl-4-hydroxybenzylidene)-3,4-dihydro-3-oxo-2H-1, 4-benzothiazine (0.83 g) dissolved in tetrahydrofuran (6 ml) was added dropwise under ice-cooling and argon atmosphere. The mixture was stirred for 15 minutes at room temperature. Bromoacetonitrile (0.17 ml) dissolved in tetrahydrofuran (2 ml) was added to the mixture, and the mixture was stirred overnight at room temperature. To the mixture, 0.5 N hydrochloric acid was added, and the whole was extracted with ethyl acetate. The organic layer was washed with saturated sodium chloride solution, dried over anhydrous sodium sulfate and concentrated in vacuo. The oily residue was purified by silica gel column chromatography to give 0.26 g (28.4%) of the titled compound.

mp 152.6°–153.4° C. (benzene-diisopropyl ether)

IR (KBr, cm$^{-1}$) 3630, 2961, 2243, 1666, 1593, 1485, 1421, 1363, 1263, 1226, 1198, 905, 756

The following compounds can be prepared by a method similar to Example 1.

2-[5-tert.-Butyl-3-[1,1-dimethyl-2-(tetrahydropyran-2-yloxy) ethyl]-4-hydroxybenzylidene]-4-cyanomethyl-3,4-dihydro-3-oxo-2H-1,4-benzothiazine (compound No. 1-2)

IR (KBr, cm$^{-1}$) 3206, 2951, 2872, 2250, 1655, 1590, 1486, 1422, 1390, 1263, 1203, 1122, 1035, 749

2-(4-Acetoxy-3,5-diisopropylbenzlidene)-4-cyanomethyl-3,4-dihydro-3-oxo-2H-1,4-benzothiazine (compound No. 1-3)

mp 175.7°–177.1° C.

IR (KBr, cm$^{-1}$) 2962, 2203, 1756, 1658, 1595, 1486, 1445, 1363, 1264, 1211, 1164, 1120, 918, 747

2-(3,5-Di-tert.-butyl-4-hydroxybenzylidene)-4-(3-cyanopropyl)-3,4-dihydro-3-oxo-2H-1,4-benzothiazine (compound No. 1-4)

2-(3,5-Di-tert.-butyl-4-hydroxybenzylidene)-4-(7-cyanoheptyl)-3,4-dihydro-3-oxo-2H-1,4-benzothiazine (compound No. 1-5)

2-(3-tert.-Butyl-4-hydroxybenzylidene)-4-cyanomethyl-3,4-dihydro-3-oxo-2H-1,4-benzothiazine (compound No. 1-6)

4-Cyanomethyl-3,4-dihydro-2-(4-hydroxy-3,5dimethyl-benzylidene)-3-oxo-2H-1,4-benzothiazine (compound No. 1-7)

4-Cyanomethyl-3,4-dihydro-2-(4-hydroxy-5-methoxy-3methylbenzylidene)-3-oxo-2H-1,4-benzothiazine (compound No. 1-8)

2-(5-tert.-Butyl-4 -hydroxy-3 -dimethylaminomethylbenzylidene)-4-cyanomethyl-3,4-dihydro-3-oxo-2H-1,4-benzothiazine (compound No. 1-9)

2-(3,5-Di-tert.-butyl-4-methoxymethoxybenzylidene)-4-cyanomethyl-3,4-dihydro-3-oxo-2H-1,4-benzothiazine (compound No. 1-10)

2-(4-Benzyloxymethoxy-3,5-di-tert.-butylbenzylidene)-4- cyanomethyl-3,4-dihydro-3-oxo-2H-1,4-benzotniazine (compound No. 1-11)

2-(3,5 -Di-tert.- butyl-4 -trimethylsilyloxybenzylidene)-4-cyanomethyl-3,4-dihydro-3-oxo-2H-1,4-benzothiazine (compound No. 1-12)

Example 2

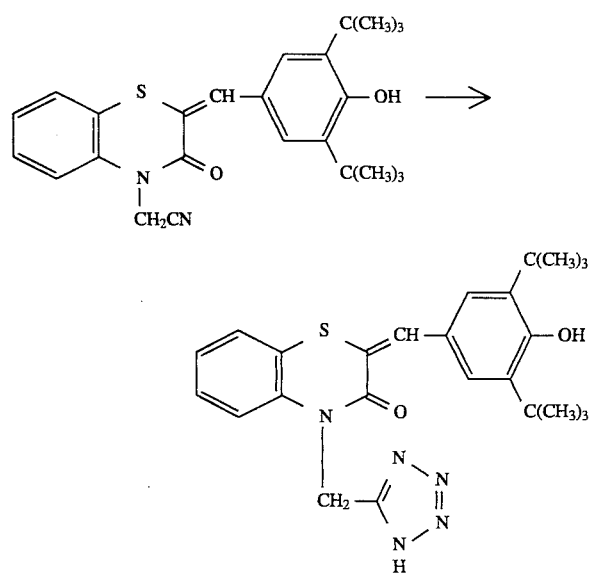

2-(3,5-Di-tert.-butyl-4-hydroxybenzylidene)-3,4-dihydro-3-oxo-4-(1H-tetrazol-5-ylmethyl)-2H-1,4-benzothiazine (compound No. 2-1)

To a solution of 2-(3,5-di-tert.-butyl-4-hydroxybenzylidene) -4-cyanomethyl-3,4-dihydro-3-oxo-2H-1,4-benzothiazine (compound No. 1-1, 0.335 g) in dimethylformaldehyde (5 ml), sodium azide (0.078 g) and ammonium chloride (0.064 g) were added. The mixture was stirred overnight at 105° C. under a nitrogen atmosphere. To the mixture, water was added, and the whole was extracted with ethyl acetate. The organic layer was dried over anhydrous sodium sulfate and concentrated in vacuo. To the oily residue, 1N aqueous sodium hydroxide solution was added. The mixture was washed with diethyl ether, acidified with 2N hydrochloric acid and extracted with ethyl acetate. The organic layer was washed with saturated sodium chloride solution, dried over anhydrous sodium sulfate and concentrated in vacuo. The oily residue was purified by silica gel column chromatography to give 0.21 g (56.9%) of the titled compound.

IR (KBr, cm$^{-1}$) 3619, 2958, 1644, 1588, 1485, 1438, 1422, 1364, 1265, 1198, 750

The following compounds can be prepared by a method similar to Example 2.

2-[5-tert.-Butyl-4-hydroxy-3-[1,1-dimethyl-2-(tetrahydropyran-2-yloxy) ethyl)benzylidene]-3,4-dihydro-3-oxo-4-(1H-tetrazol-5-ylmethyl)-2H-1,4-benzothiazine (compound No. 2-2)

IR (KBr, cm$^{-1}$) 3213, 2949, 1651, 1588, 1486, 1423, 1389, 1264, 1203, 1122, 1036, 748

2-(3,5-Di-tert.-butyl-4-hydroxybenzylidene)-3,4-dihydro-3-oxo-4-[3-(1H-tetrazol-5-yl) propyl]-2H-1,4-benzothiazine (compound No. 2-3)

2-(3,5-Di-tert.-butyl-4-hydroxybenzylidene)-3,4-dihydro-3-oxo-4-[7-(1H-tetrazol-5-yl)heptyl]-2H-1,4-benzothiazine (compound No. 2-4)

2-(3-tert.-Butyl-4-hydroxybenzylidene)-3,4-dihydro-3-oxo-4-(1H-tetrazol-5-ylmethyl)-2H-1,4-benzothiazine (compound No. 2-5)

3,4-Dihydro-2-(4-hydroxy-3,5-dimethylbenzylidene)-3-oxo-4-( 1H-tetrazol-5-ylmethyl)-2H-1,4-benzothiazine (compound No. 2-6)

3,4-Dihydro-2-(4-hydroxy-5-methoxy-3-methylbenzylidene)-3-oxo-4-(1H-tetrazol-5-ylmethyl)-2H-1,4-benzothiazine (compound No. 2-7)

2-(5-tert.-Butyl-4-hydroxy-3-dimethylaminomethylbenzylidene)-3,4-dihydro-3-oxo-4-(1H-tetrazol-5-ylmethyl)-2H-1,4-benzothiazine (compound No. 2-8)

2-(3,5-Di-tert.-butyl-4-methoxymethoxybenzylidene)-3,4-dihydro-3-oxo-4-(1H-tetrazol-5-ylmethyl)-2H-1,4-benzothiazine (compound No. 2-9)

2-(4-Benzyloxymethoxy-3,5-di-tert.-butylbenzylidene)-3,4-dihydro-3-oxo-4-(1H-tetrazol-5-ylmethyl)-2H-1,4-benzothiazine (compound No. 2-10)

2-(3,5-Di-tert.-butyl-4-trimethylsilyloxybenzylidene)-3,4-dihydro-3-oxo-4-(1H-tetrazol-5-ylmethyl)-2H-1,4-benzothiazine (compound No. 2-11)

Example 3

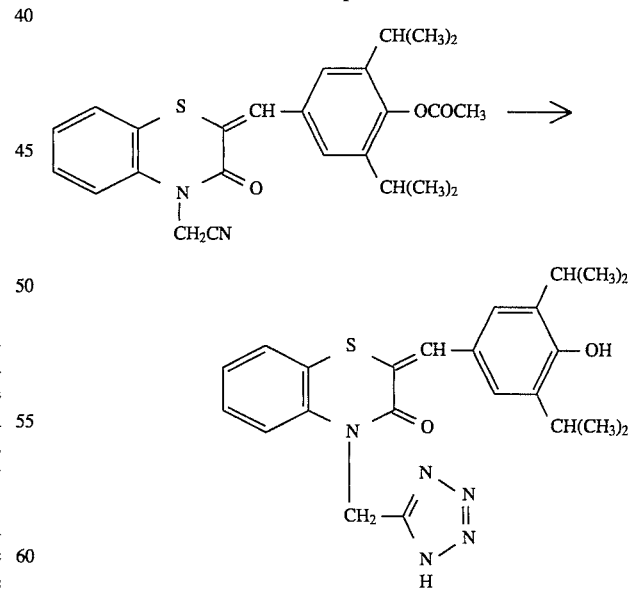

3,4-Dihydro-2-(4-hydroxy-3,5diisopropylbenzylidene)-3-oxo-4(1H-tetrazol-5-ylmethyl)-2H-1,4-benzothiazine (compound No. 3-1)

To a solution of 2-(4-acetoxy-3,5-diisopropylbenzylidene)-4-cyanomethyl-3,4-dihydro-3-oxo-2H-1,4-benzothiazine (compound No. 1-3, 0.47 g) in dimethylformaldehyde (5 ml), sodium azide (0.21 g) and ammonium chloride (0.17 g) were added. The mixture was stirred overnight at 105° C. under a nitrogen atmosphere. To acidify the mixture, 1N hydrochloric acid was added. Saturated sodium chloride solution was added to the mixture and the whole was extracted with ethyl acetate. The organic layer was dried over anhydrous sodium sulfate and concentrated in vacuo. To the residue, 1N aqueous sodium hydroxide solution was added and the whole was washed with diethyleter. 5.8N hydrochloric acid was added to the aqueous layer to acidify it and the whole was extracted with ethyl acetate. The organic layer was washed with saturated sodium chloride solution, dried over anhydrous sodium sulfate and concentrated in vacuo. The oily residue was purified by silica gel column chromatography to give 0.36 g (76.4%) of the titled compound.

mp 189.2°–190.1° C. (diisopropylether-ethyl acetate)

IR (KBr, cm$^{-1}$) 3452, 2959, 2607, 1649, 1591, 1467, 1442, 1367, 1317, 1279, 1261, 1223, 1179, 1135, 918, 762

Example 4

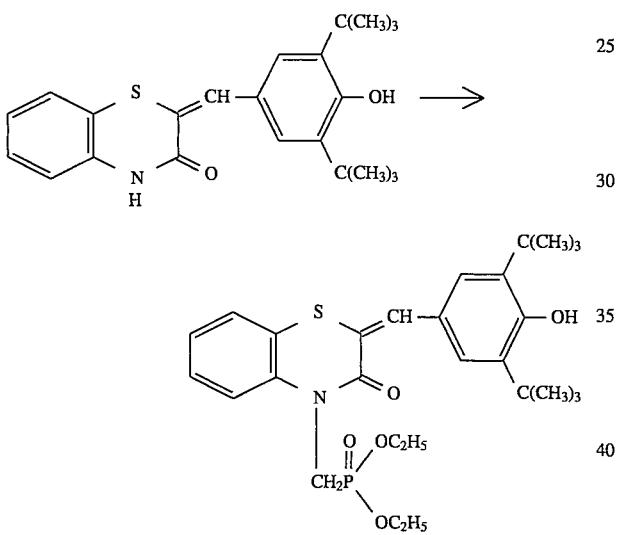

2-(3,5-Di-tert.-butyl-4-hydroxybenzylidene)-4-phosphonylmethyl-3,4-dihydro-3-oxo-2H-1,4-benzothiazine diethyl ester (compound No. 4-1)
method 1

To a suspension of sodium hydride (60% suspension in mineral oil, 0.42 g) in tetrahydrofuran (20 ml), 2-(3,5-di-tert.-butyl-4-hydroxybenzylidene)-3,4-dihydro-3-oxo-2H-1,4-benzothiazine (2.00 g) dissolved in tetrahydrofuran (20 ml) was added, dropwise, under ice-cooling and a nitrogen atmosphere. The mixture was stirred for 40 minutes at room temperature. To the mixture, (chloromethyl)methylether (0.51 g) dissolved in tetrahydrofuran (10 ml) was added dropwise, and the mixture was stirred further for 15 hours at room temperature. Water was added to the mixture and the whole was extracted with ethyl acetate. The organic layer was washed with saturated sodium chloride solution, dried over anhydrous sodium sulfate and concentrated in vacuo. The oily residue was purified by silica gel column chromatography to give 0.61 g (27.2%) of 2-(3,5-di-tert.-butyl-4-hydroxybenzylidene)-3,4-dihydro-4-methoxymethyl-3-oxo-2H-1,4-benzothiazine.

mp 138.9°–139.4° C.

IR (KBr, cm$^{-1}$) 3552, 2953, 1653, 1590, 1559, 1441, 1364, 1253, 1207, 1116, 1071, 744
method 2:

To a solution of 2-(3,5-di-tert.-butyl-4-hydroxybenzylidene)-3,4-dihydro-4-methoxymethyl-3-oxo-2H-1,4-benzothiazine (1.00 g ), prepared by the method 1, in chloroform (10 ml ), trimethylsilyl iodide (0.43 ml ) was added dropwise under a nitrogen atmosphere. The mixture was stirred for 3 hours at room temperature. To the mixture, triethylphosphite (4.01 ml) was added and the mixture was stirred further for 20 minutes at room temperature. Water was added to the mixture and the whole was extracted with ethyl acetate. The organic layer was washed with saturated sodium chloride solution, dried over anhydrous magnesium sulfate and concentrated in vacuo. The oily residue was purified by silica gel column chromatography to give 0.33 g (26.3% ) of the titled compound.

mp 94.0°–95.3° C.

IR (KBr, cm$^{-1}$) 3396, 2956, 1649, 1589, 1484, 1438, 1265, 1232, 1026, 752

The following compounds can be prepared by a method similar to Example 4.

4-Diethoxyphosphorylmethyl-3,4-dihydro-2-(4-hydroxy-3,5-diisopropylbenzylidine)-3-oxo-2H-1,4-benzothiazine (compound No. 4-2)

mp 144.8°–146.0° C.

IR (KBr, cm$^{-1}$) 3298, 2959, 1641, 1590, 1569, 1468, 1445, 1358, 1326, 1283, 1264, 1241, 1193, 1049, 1016

2-(3-tert.-Butyl-4-hydroxybenzylidene)-4-phosphonylmethyl-3,4-dihydro-3-oxo-2H-1,4-benzothiazine diethyl ester- (compound No. 4-3 )

4-Diethoxyphosphorylmethyl-3,4-dihydro-2-(4-hydroxy-3, 5dimethylbenzylidene)-3-oxo-2H-1,4-benzothiazine (compound No. 4-4)

2-(5-tert.-Butyl-4-hydroxy-3-dimethylaminomethylbenzylidene)- 4-phosphonylmethyl-3,4-dihydro-3-oxo-2H-1,4-benzothiazine diethyl ester (compound No. 4-5)

Example 5

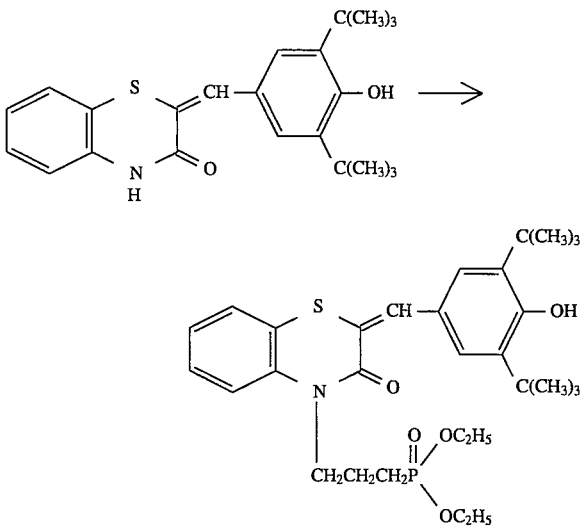

2-(3,5-Di-tert.-butyl-4-hydroxybenzylidene)-4-(3-phosphonylmethyl-3,4-dihydro-3-oxo-2H-1,4-benzothiazine diethyl ester (compound No. 5-1)

To a suspension of sodium hydride (60% suspension in paraffin liquid, 0.06 g) in tetrahydrofuran (2 ml), 2-(3,5-ditert.-butyl-4-hydroxybenzylidene)-3,4-dihydro-3-oxo-2H-1, 4-benzothiazine (0.27 g) dissolved in tetrahydrofuran (4 ml) was added, dropwise, under ice-cooling and a nitrogen atmosphere. The mixture was stirred for 15 minutes at room temperature. To the mixture, diethyl 3-chloropropylphosphate (0.23 g) dissolved in tetrahydrofuran (2 ml) was added and the mixture was stirred overnight at 40° C. Saturated aqueous ammonium chloride solution was added to the mixture and the whole was extracted with ethyl acetate. The organic layer was dried over anhydrous magnesium sulfate and concentrated in vacuo. The oily residue was purified by silica gel column chromatography to give the titled compound.

The following compound can be prepared by a method similar to Example 5.

2-(3,5-Di-tert.-butyl-4-hydroxybenzylidine)-4-(7-diethoxyphosphorylheptyl)-3,4-dihydro-3 -oxo-2H-1,4-benzothiazine (compound No. 5-2)

Example 6

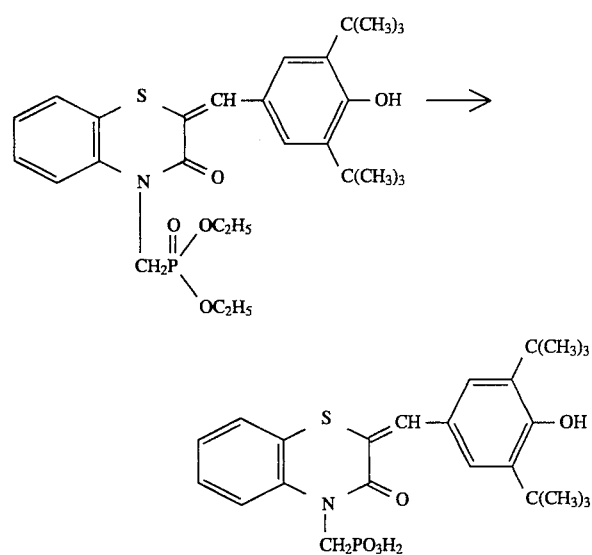

2-(3,5-Di-tert.-butyl-4-hydroxybenzylidene)-3,4-dihydro-3-oxo-4-phosphonomethyl-2H-1,4-benzothiazine (compound No. 6-1)

2-(3,5-Di-tert.-butyl-4-hydroxybenzylidene)-4-phosphonylmethyl-3,4-dihydro-3-oxo-2H-1,4-benzothiazine diethyl ester- (compound No. 4-1, 0.35 g) was dissolved in a mixture of dioxane (6 ml) and 5.8 N hydrochloric acid (6 ml). The mixture was refluxed for 50 minutes. After cooling to room temperature, 1N hydrochloric acid was added to the mixture and the whole was extracted with chloroform. The organic layer was washed with saturated sodium chloride solution, dried over anhydrous magnesium sulfate and concentrated in vacuo. Diisopropyl ether and cyclohexane were added to crystallize the oily residue and to give 0.14 g (43.5%) of the titled compound.

mp 232.5°–233.0° C. (n-hexan-ethyl acetate, dec.)

IR (KBr, cm$^{-1}$) 3607, 2960, 1630, 1593, 1434, 1367, 1217, 1144, 940

The following compounds can be prepared by a method similar to Example 6.

2-(4-Hydroxy-3,5-diisopropylbenzylidene)-3,4-dihydro-3-oxo-4-phosphonomethyl-2H-1,4-benzothiazine (compound No. 6-2)

IR (Film, cm$^{-1}$) 3421, 2962, 1633, 1587, 1469, 1372, 1266, 1199, 1174, 908, 733

2-(3,5-Di-tert.-butyl-4-hydroxybenzylidene)-3,4-dihydro-3-oxo-4-(3-phosphonopropyl)-2H-1,4-benzothiazine (compound No. 6-3)

2-(3,5-Di-tert.-butyl-4-hydroxybenzylidene)-3,4-dihydro-3-oxo-4-(7-phosphonoheptyl)-2H-1,4-benzothiazine (compound No. 6-4)

2-(3-tert.-Butyl-4-hydroxybenzylidene)-3,4-dihydro-3-oxo-4-phosphonomethyl-2H-1,4-benzothiazine (compound No. 6-5)

3,4-Dihydro-2-(3,5-dimethyl-4-hydroxybenzylidene)-3-oxo-4-phosphonomethyl-2H-1,4-benzothiazine (compound No. 6-6)

2 -(5-tert.-Butyl-4-hydroxy-3-dimethylaminomethylbenzylidene)-3,4-dihydro-3-oxo-4-phosphonomethyl-2H-1,4-benzothiazine (compound No. 6-7)

Example 7

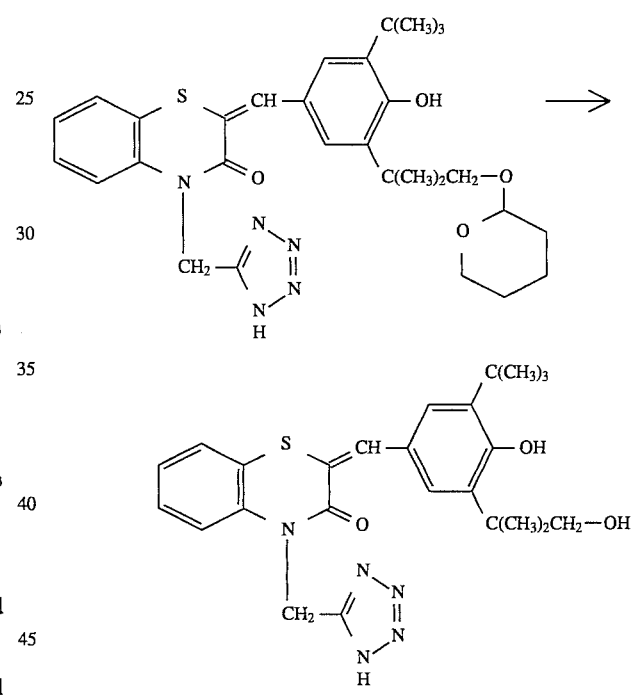

2-[5-tert.-Butyl-3-(2-hydroxy-1,1-dimethylethyl)-4hydroxybenzylidene]-3,4-dihydro-3-oxo-4-(1H-tetrazol-5-ylmethyl)-2H-1, 4 -benzothiazine (compound No. 7-1)

2-[5-tert.-Butyl-4-hydroxy-3-[1,1-dimethyl-2-(tetrahydropyran-2-yloxy)ethyl]benzylidene]-3,4-dihydro-3-oxo-4-(1H-tetrazol-5-ylmethyl)-2H-1,4-benzothiazine (compound No. 2-2, 0.31 g) was dissolved in a mixture of methanol (5 ml) and chloroform (1 ml). To the mixture, p-toluenesulfonic acid monohydrate (0.05 g) was added and the mixture was stirred for 3 hours at 60° C. Saturated sodium chloride solution was added to the mixture and the whole was extracted with ethyl acetate. The organic layer was washed with saturated sodium chloride solution, dried over anhydrous magnesium sulfate and concentrated in vacuo. The oily residue was purified by silica gel column chromatography to give 0.16 g (60.7%) of the titled compound.

IR (KBr, cm$^{-1}$) 3106, 2961, 1629, 1586, 1486, 1422, 1369, 1265, 1190, 1047, 750

Example 8

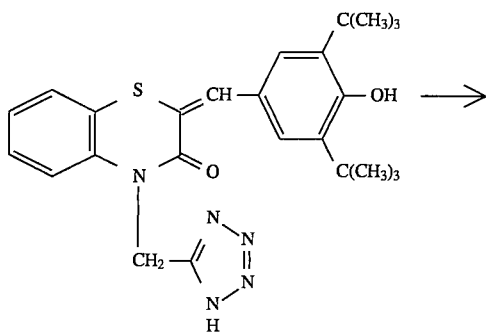

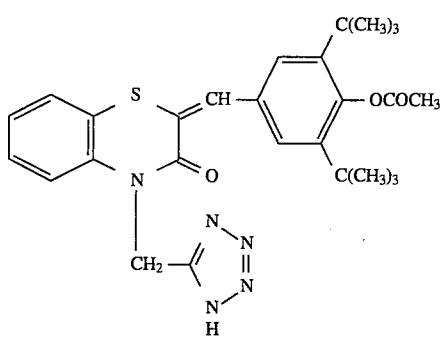

2-(4-Acetoxy-3,5-di-tert.-butylbenzylidene)-3,4-dihydro-3-oxo-4(1H-tetrazol-5-ylmethyl)-2H-1,4-benzothiazine (compound No. 8-1)

Acetic anhydride (5.8 ml) and triethylamine (2.1 ml) were added to 2-(3,5-di-tert.-butyl-4-hydroxybenzylidene)-3,4-dihydro-3-oxo-4-(1H-tetrazol-5-ylmethyl)-2H-1,4-benzothiazine (compound No. 2-1, 0.32 g) and the mixture was refluxed overnight. To the mixture, dilute hydrochloric acid was added and the whole was extracted with ethyl acetate. The organic layer was dried over anhydrous sodium sulfate and concentrated in vacuo. The oily residue was purified by silica gel column chromatography to give the titled compound.

The following compounds can be prepared by a method similar to Example 8.

2-(4-Benzoyloxy-3,5-di-tert.-butylbenzylidene)-3,4-dihydro-3-oxo-4-(1H-tetrazol-5-ylmethyl)-2H-1,4-benzothiazine (compound No. 8-2)

2-(4-Acetoxy-3,5-di-tert.-butylbenzylidene)-3,4-dihydro-3-oxo-4-phosphonomethyl-2H-1,4-benzothiazine (compound No. 8-3)

2-(4-Benzoyloxy-3,5-di-tert.-butylbenzylidene)-3,4-dihydro-3-oxo-4-phosphonomethyl-2H-1,4-benzothiazine (compound No. 8-4)

Example 9

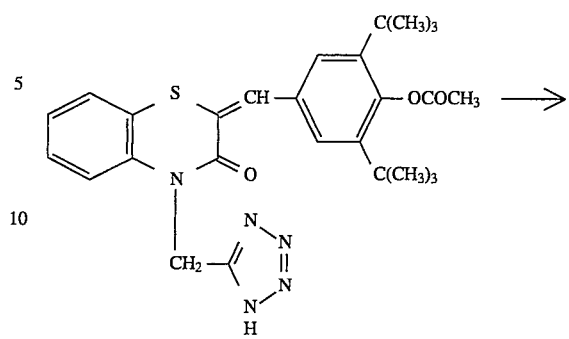

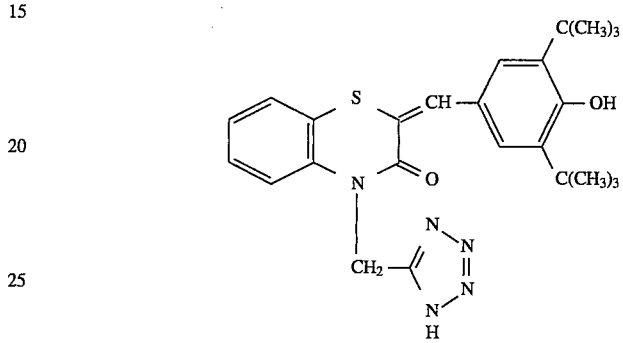

2-(3,5-Di-tert.-butyl-4-hydroxybenzylidene)-3,4-dihydro-3-oxo-4(1H-tetrazol-5-ylmethyl)-2H-1,4-benzothiazine (compound No. 2-1)

To a solution of 2-(4-acetoxy-3,5-di-tert.-butylbenzylidene)-3,4-dihydro-3-oxo-4-(1H-tetrazol-5-ylmethyl)2H-1,4-benzothiazine (compound No. 8-1, 0.19 g) in ethanol (10 ml), potassium hydroxide (0.58 g) dissolved in water (10 ml) was added. The mixture was refluxed over night. 6N hydrochloric acid was added to the mixture to acidify it. The mixture was concentrated in vacuo and extracted with ethyl acetate. The organic layer was dried over anhydrous sodium sulfate and concentrated in vacuo. The oily residue was purified by silica gel column chromatography to give the titled compound. The physical property of the compound obtained above was the same as the compound (No. 2-1) prepared in Example 2.

Example 10

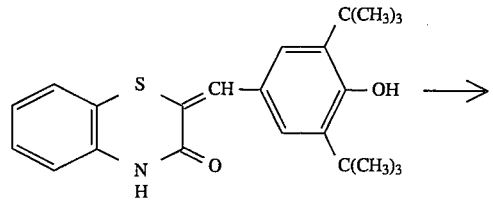

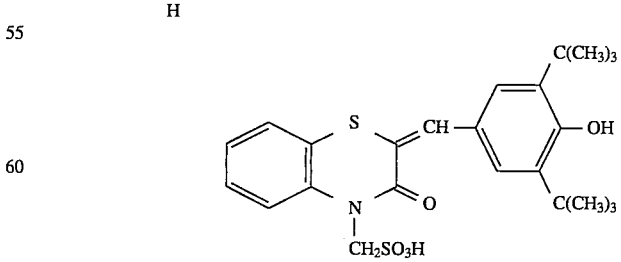

2-(3,5-Di-tert.-butyl-4-hydroxybenzylidene)-3,4-dihydro-3-oxo-4-sulfomethyl-2H-1,4-benzothiazine (compound No. 10-1)

To a suspension of sodium hydride (60% suspension in paraffin liquid, 0.042 g) in dimethylformaldehyde (1 ml), 2-(3, 5-di-tert.-butyl-4-hydroxybenzylidene)-3,4-dihydro-3-oxo-2H-1,4-benzothiazine (0.20 g) dissolved in dimethylformalhyde (2 ml) was added, dropwise, under ice-cooling and a nitrogen atmosphere. The mixture was stirred for 40 minutes at room temperature. To the mixture, potassium (chloro)methanesulfonate (0.096 g) dissolved in dimethylformaldehyde (2 ml) was added, dropwise, and the mixture was stirred for one day at room temperature. 1N hydrochloric acid was added to the mixture and the whole was extracted with ethyl acetate. The organic layer was washed with saturated sodium chloride solution, dried over anhydrous sodium sulfate and concentrated in vacuo. The oily residue was purified by silica gel column chromatography to give the titled compound.

FORMULATION

Examples of the formulations of the compounds of this invention are shown below.

Tablet

| | |
|---|---|
| compound of this invention | 1 mg |
| lactose | 131 mg |
| crystalline cellulose | 35 mg |
| hydroxypropylcellulose | 2 mg |
| magnesium stearate | 1 mg |
| total | 170 mg |
| compound of this invention | 50 mg |
| lactose | 140 mg |
| crystalline cellulose | 45 mg |
| polyvinylpyrrolidone | 3 mg |
| magnesium stearate | 2 mg |
| total | 240 mg |

Granule

| | |
|---|---|
| compound of this invention | 100 mg |
| lactose | 390 mg |
| polyvinylpyrrolidone | 8 mg |
| magnesium stearate | 2 mg |
| total | 500 mg |

Eye Drops

| | |
|---|---|
| compound of this invention | 0.5 g |
| conc. glycerol | 1.5 g |
| hydrogenated castor oil | 1.0 g |
| benzalkonium chloride | 0.005 g |
| sodium edetate | 0.01 g |
| dilute hydrochloric acid | q.s. |
| sodium hydroxide | q.s. |
| sterile purified water | q.s. |
| total | 100 ml |
| compound of this invention | 3.0 g |
| conc. glycerol | 1.0 g |
| polysorbate 80 | 7.0 g |
| benzalkonium chloride | 0.005 g |
| sodium edetate | 0.01 g |
| dilute hydrochloric acid | q.s. |
| sodium hydroxide | q.s. |
| sterile purified water | q.s. |
| total | 100 ml |
| compound of this invention | 0.01 g |
| conc. glycerol | 2.0 g |
| polysorbate 80 | 0.5 g |
| benzalkonium chloride | 0.005 g |
| sodium edetate | 0.01 g |
| dilute hydrochloric acid | q.s. |
| sodium hydroxide | q.s. |
| sterile purified water | q.s. |
| total | 100 ml |

Eye Ointment

| | |
|---|---|
| compound of this invention | 1.0 g |
| liquid parafine | 10.0 g |
| white petrolatum | 89.0 g |
| total | 100.0 g |

PHARMACOLOGICAL TEST

In order to study the utility of the compounds of this invention, the protein stabilizing effect and the suppressive effect on lipid peroxide formation were examined.

1. Protein Stabilizing Effect

As a method of examining the protein stabilizing effect, a method for measuring an effect of a compound on the stability of bovine serum albumin against heat coagulation is known (Lancet, 1, 169 (1965)).

The protein stabilizing effect of the compound of this invention was examined according to the method described in the above-mentioned journal.

Experimental Method

Under ice cooling, bovine serum albumin (Sigma Chemical Company) was dissolved in 0.2M potassium phosphate buffer solution (pH 5.3) to adjust the concentration to 0.75%. To 2.7 ml of this albumin solution, 0.3 ml of a solution of a test compound in dimethyl sulfoxide was added and stirred. The reaction mixture was allowed to stand for 15 minutes at room temperature. After the solution was shaken for 2 minutes in a water bath at 67° C., the reaction was stopped by ice cooling. The temperature of the reaction mixture was raised to room temperature, and the absorbance, which is related to the white turbidity of water-soluble protein caused by heat coagulation, was measured at 660 nm of wave length.

As a reference compound, 2-(3,5-di-tert.-butyl-4-hydroxybenzylidene)-3,4-dihydro-4-methyl-3-oxo-2H-1,4-benzothiazine, which was described in Japanese Unexamined Patent Publication No. 287077/1989, was used. The protein stabilizing effect of the compound of this invention was calculated by the following Formula.

$$\text{Protein stabilizing effect (\%)} = \frac{A_0 - A_1}{A_0} \times 100$$

$A_0$: absorbance in the case of absence of a test compound $A_1$: absorbance in the case of presence of a test compound

Result

The experimental results are shown in Table 1.

TABLE 1

| Test compound | Concentration of test compound | Protein stabilizing effect |
|---|---|---|
| Reference compound | $10^{-4}M$ | −30.1% |
| Compound No. 2-1 | $10^{-4}M$ | 84.8% |
| Compound No. 6-1 | $10^{-4}M$ | 98.8% |

The compounds of this invention inhibited the heat coagulation of protein significantly and showed excellent protein stabilizing effect. But the reference compound did not show a protein stabilizing effect, and a tendency to accelerate the heat coagulation of protein was observed.

2. Suppressive Effect on Lipid Peroxide Formation

Experimental Method

In 0.04M Tris buffer (containing 0.09M of potassium chloride, pH 7.4) containing a test compound, microsomes of rat liver, which was prepared according to Biochimica et Biophysica Acta, 618 (1980) 35–41, were reacted with ADP (13.2 mM), $Fe^{2+}$ (0.9 mM) and ascorbic acid (0.5 mM) for 15 minutes at 37° C. The amount of the produced lipid peroxide was measured by TBA method (Yagi et al., Blochem. Med., 15, 212 (1976)).

Result

The experimental results are shown in Table 2.

TABLE 2

| Test compound | Concentration of test compound | Suppressive effect on lipid peroxide formation |
|---|---|---|
| Compound No. 2-1 | $10^{-5}M$ | 100.0% |
| Compound No. 6-1 | $10^{-5}M$ | 100.0% |

As shown in Table 2, each compound of this invention showed an excellent suppressive effect on lipid peroxide formation.

As shown in the results of the above Pharmacological Tests, the compound of this invention has both a protein stabilizing effect and a suppressive effect on lipid peroxide formation and it is expected that the compounds of this invention will be an excellent therapeutic agent for cataracts.

What we claim is:

1. A compound having the following formula (I) or salt thereof,

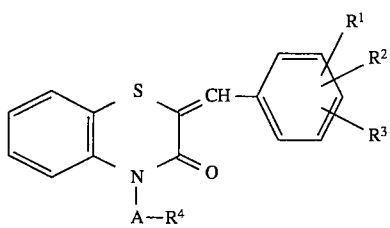

wherein $R^1$ is hydroxy which can be protected by a protective group;

$R^2$ is lower alkyl;

$R^3$ is hydrogen; a substituted or unsubstituted lower alkyl; hydroxy; hydroxy protected by a protective group; or lower alkoxy; wherein said substituted lower alkyl is substituted by hydroxy; hydroxy protected by a protective group; amino; or lower alkylamino;

$R^4$ is tetrazolyl, phosphono or lower alkyl ester thereof, or sulfonyl or lower alkyl ester thereof, and A is alkylene having 1 to 10 carbon atoms.

2. A compound having the following formula (I) or a salt thereof,

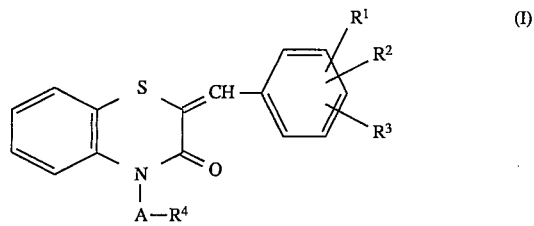

wherein $R^1$ is hydroxy, lower alkysulfonyloxy, phenylsulfonyloxy, toluenesulfonyloxy, xylylsulfonyloxy, mesitylsulfonyloxy, lower alkanoyloxy, lower alkoxymethyloxy, benzoyloxy, benzyloxymethyloxy, tetrahydropyranyloxy or trimethylsilyloxy;

$R^2$ is lower alkyl;

$R^3$ is hydrogen, substituted or unsubstituted lower alkyl, hydroxy, lower alkylsulfonyloxy, phenylsulfonyloxy, toluenesulfonyloxy, xylylsulfonyloxy, mesitylsulfonyloxy, lower alkanoyloxy, benzoyloxy, lower alkoxymethyloxy, benzyloxymethyloxy, tetrahydropyranyloxy, trimethylsilyloxy or lower alkoxy, wherein said substituted lower alkyl is substituted by hydroxy, lower alkylsulfonyloxy, phenylsulfonyloxy, toluenesulfonyloxy, xylylsulfonyloxy, mesitylsulfonyloxy, lower alkanoyloxy, benzoyloxy, lower alkoxymethyloxy, benzyloxymethyloxy, tetrahydropyranyloxy, trimethylsilyloxy, amino or lower alkylamino;

$R^4$ is tetrazolyl, phosphono or lower alkyl ester thereof, or, sulfonyl or lower alkyl ester thereof, and A is alkylene having 1 to 10 carbon atoms.

3. The compound or a salt thereof as claimed in claim 2, wherein $R^1$ is hydroxy.

4. The compound or a salt thereof as claimed in claim 2, wherein $R^1$ is hydroxy; $R^3$ is lower alkyl or hydroxy lower alkyl.

5. The compound or a salt thereof as claimed in claim 2, wherein $R^1$ is hydroxy; $R^3$ is lower alkyl or hydroxy lower alkyl; $R^4$ is tetrazolyl, phosphono or sulfonyl.

6. 2-(3,5-Di-tert.-butyl-4-hydroxybenzylidene)-3,4-dihydro-3-oxo-4-phosphonomethyl-2H-1,4-benzothiazine.

7. 2-(3,5-Di-tert.-butyl-4-hydroxybenzylidene)-3, 4-dihydro-3-oxo-4-(1H-tetrazol-5-ylmethyl)-2H-1,4-benzothiazine.

8. 2-[5-tert.-Butyl-3-(2-hydroxy-1,1-dimethylethyl)-4-hydroxybenzylidene]-3,4-dihydro-3-oxo-4-(1H-tetrazol-5ylmethyl)-2H-1,4-benzothiazine.

9. A pharmaceutical composition comprising a compound as claimed in claim 1 or a salt thereof and pharmaceutically acceptable carrier.

10. A method for treatment of cataract which comprises administering an effective amount of the composition as claimed in claim 9.

11. A compound having the following formula (II) or a salt thereof,

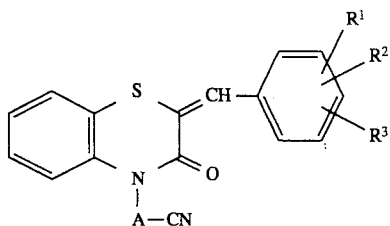

wherein
R¹ is hydroxy which can be protected by a protective group;
R² is lower alkyl;
R³ is hydrogen; a substituted or unsubstituted lower alkyl; hydroxy; hydroxy protected by a protective group; or lower alkoxy; wherein said substituted lower alkyl is substituted by hydroxy; hydroxy protected by a protective group; amino; or lower alkylamino; and
A is alkylene having 1 to 10 carbon atoms.

12. A compound having the following formula (II) or a salt thereof,

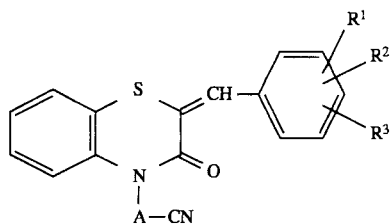

wherein
R¹ is hydroxy, lower alkylsulfonyloxy, phenylsulfonyloxy, toluenesulfonyloxy, xylylsulfonyloxy, mesitylsulfonyloxy, lower alkanoyloxy, lower alkoxymethyloxy, benzoyloxy, benzyloxymethyloxy, tetrahydropyranyloxy or trimethylsilyloxy;
R² is lower alkyl;
R³ is hydrogen, substituted or unsubstituted lower alkyl, hydroxy, lower alkylsulfonyloxy, phenylsulfonyloxy, toluenesulfonyloxy, xylylsulfonyloxy, mesitylsulfonyloxy, lower alkanoyloxy, benzoyloxy, lower alkoxymethyloxy, benzyloxymethyloxy, tetrahydropyranyloxy, trimethylsilyloxy or lower alkoxy, wherein said substituted lower alkyl is substituted by hydroxy, lower alkylsulfonyloxy, phenylsulfonyloxy, toluenesulfonyloxy, xylylsulfonyloxy, mesitylsulfonyloxy, lower alkanoyloxy, benzoyloxy, lower alkoxymethyloxy, benzyloxymethyloxy, tetrahydropyranyloxy, trimethylsilyloxy, amino or lower alkylamino; and 13. The compound or a salt thereof as claimed in claim 12, wherein R¹ is hydroxy.

14. The compound or a salt thereof as claimed in claim 12, wherein R¹ is hydroxy; R³ is lower alkyl or hydroxy lower alkyl.

15. 2-(3,5-Di-tert.-butyl-4-hydroxybenzylidene)-4-cyanomethyl3,4-dihydro-3-oxo-2H-1,4-benzothiazine.

* * * * *